(12) United States Patent
Boese et al.

(10) Patent No.: US 7,794,446 B2
(45) Date of Patent: Sep. 14, 2010

(54) METHOD OF RECORDING TWO-DIMENSIONAL IMAGES OF A PERFUSED BLOOD VESSEL

(75) Inventors: Jan Boese, Eckental (DE); Martin Kleen, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 983 days.

(21) Appl. No.: 11/062,302

(22) Filed: Feb. 18, 2005

(65) Prior Publication Data

US 2005/0203424 A1 Sep. 15, 2005

(30) Foreign Application Priority Data

Feb. 20, 2004 (DE) ............... 10 2004 008 367

(51) Int. Cl.
*A61M 31/00* (2006.01)
*A61B 6/00* (2006.01)
*A61B 1/12* (2006.01)

(52) U.S. Cl. ............... 604/508; 604/500; 604/507; 600/478; 600/156

(58) Field of Classification Search ............... 604/478, 604/500, 507, 28, 508; 600/478, 156, 431, 600/435, 433
See application file for complete search history.

(56) References Cited

U.S. PATENT DOCUMENTS

| | | | | |
|---|---|---|---|---|
| 4,329,986 | A * | 5/1982 | Babb | 604/5.04 |
| 5,084,011 | A * | 1/1992 | Grady | 604/24 |
| 5,181,518 | A * | 1/1993 | McDonagh | 600/508 |
| 6,470,209 | B2 * | 10/2002 | Snoke | 600/478 |
| 6,537,246 | B1 * | 3/2003 | Unger et al. | 604/82 |
| 6,551,302 | B1 | 4/2003 | Rosinko et al. | |
| 6,659,949 | B1 * | 12/2003 | Lang et al. | 600/438 |
| 6,673,039 | B1 * | 1/2004 | Bridges et al. | 604/96.01 |
| 6,836,528 | B2 * | 12/2004 | Reddy et al. | 378/5 |
| 6,869,440 | B2 * | 3/2005 | Dobak, III | 607/105 |
| 7,300,429 | B2 * | 11/2007 | Fitzgerald et al. | 604/508 |
| 2002/0016621 | A1 * | 2/2002 | Werneth et al. | 607/105 |
| 2002/0049484 | A1 * | 4/2002 | Werneth et al. | 607/105 |
| 2003/0157024 | A1 * | 8/2003 | Tachibana et al. | 424/9.52 |

(Continued)

FOREIGN PATENT DOCUMENTS

EP 0 904 797 A2 3/1999

(Continued)

OTHER PUBLICATIONS

Brezinski, "Characterizing arterial plaque with optical coherence tomography", Current Opinion in Cardiology 17, 2002, pp. 648-655, ISSN 02684705, Lippincott Williams & Wilkins, Inc.

(Continued)

*Primary Examiner*—Kevin C. Sirmons
*Assistant Examiner*—Michael J Anderson

(57) ABSTRACT

The invention relates to a method for recording two-dimensional images on the interior of a perfused blood vessel by means of optical coherence tomography using a catheter with an integrated imaging device, via which light is radiated and light reflected from the vascular wall is recorded, whereby a fluid containing a medium having a higher refractive index than blood plasma and/or cytoplasm is injected, via the catheter, into the vascular area to be recorded, to enable imaging to be carried out, whereby said fluid is a mixture of autologous blood and the medium.

8 Claims, 2 Drawing Sheets

U.S. PATENT DOCUMENTS

| | | | |
|---|---|---|---|
| 2004/0003022 A1 | 1/2004 | Garrison et al. | |
| 2004/0030220 A1 | 2/2004 | Hamm | |
| 2004/0044302 A1* | 3/2004 | Bernard et al. | 604/6.09 |
| 2005/0113686 A1* | 5/2005 | Peckham | 600/431 |
| 2005/0149002 A1* | 7/2005 | Wang et al. | 606/1 |
| 2005/0203424 A1* | 9/2005 | Boese et al. | 600/478 |
| 2005/0238586 A1* | 10/2005 | Sutton et al. | 424/9.52 |
| 2006/0116627 A1* | 6/2006 | Bridges et al. | 604/19 |

FOREIGN PATENT DOCUMENTS

| | | |
|---|---|---|
| JP | 11221229 A | 8/1999 |
| JP | 2000329534 A | 11/2000 |
| WO | 2004014233 A1 | 2/2004 |

OTHER PUBLICATIONS

Schmitt, "Optical Coherence Tomography (OCT): A Review", IEEE Journal of Selected Topics in Quantum Electronics, Jul./Aug. 1999, pp. 1205-1215, vol. 5, No. 4, 1077-260X(99)07521-8.

Brezinski et al., "Index Matching to Improve Optical Coherence Tomography Imaging Through Blood", Circulation, Journal of the American Heart Association 2001, 103, pp. 1999-2003.

* cited by examiner

METHOD OF RECORDING TWO-DIMENSIONAL IMAGES OF A PERFUSED BLOOD VESSEL

CROSS REFERENCE TO RELATED APPLICATIONS

This application claims priority to the German application No. 10 2004 008 367.3, filed Feb. 20, 2004 which is incorporated by reference herein in its entirety.

FIELD OF INVENTION

The invention relates to a method for recording two-dimensional images on the interior of a perfused blood vessel by means of optical coherence tomography using a catheter with an integrated imaging device, via which light is radiated and light reflected from the vascular wall is recorded.

BACKGROUND OF INVENTION

Optical coherence tomography (OCT) is a catheter-based tomographic procedure, which is used—among other things—for obtaining two-dimensional vascular images in vivo. The catheter-guided image recording units used are very narrow wires with integrated optical fibers, via which optical fibers light is emitted in the near infrared range (approx. 1300 nm) and the reflection from the vascular wall is registered with depth resolution by means of inferometry. By translating the radiated light beam, information is obtained from various adjacent parts of the vascular wall and combined into a two-dimensional image covering a large-area.

SUMMARY OF INVENTION

Since the blood vessel is perfused, light must always be emitted and captured through a layer of blood during an in vivo investigation. Blood is a suspension consisting mainly of red blood cells (erythrocytes) and blood plasma. Blood plasma and cytoplasm of the red blood cells have different optical refractive indexes. Because of the large number of cells in the blood (approx $5.\text{times}.10.\text{sup}.6$ g/.mu.L of blood), the many refractions can cause scattering of light and loss of energy, so that a meaningful image sometimes cannot be obtained.

In the prior art, in a known method, blood is removed from the vascular area to be investigated. This is done by deploying a transparent balloon in the vessel and positioning the fiber-mounted imaging device inside the balloon. The balloon fits tightly against the vascular wall, so that there is no blood between the balloon and the vascular wall. The light can pass unhindered to the vascular wall, and the reflected light can be returned, through the transparent medium in the balloon. The disadvantage, however, is that the incoming blood supply (in the case of an artery) or outgoing blood flow (in the case of a vein) is interrupted for the duration of the investigation. It is usually arteries that are being investigated, whereby the interruption of the blood supply is particularly problematic since organs arranged downstream of the point of interruption are no longer supplied. Moreover, the inflation of the balloon in the artery may result in some trauma. In particular, in atherosclerotically-transformed vessels (such vessels being preferred subjects of investigation), the inner vascular wall is at risk of tearing.

According to another method, a common salt solution or x-ray contrast medium is injected into the vessel during the investigation to flush out or extensively dilute the residual blood, so that the quantity of red blood cells in the blood is greatly reduced and there are fewer scattering or refraction centers. The speed of injection of the common salt solution or x-ray contrast medium must at least approximately correspond to the blood flow in the artery/vein being investigated. Yet this procedure likewise involves the transportation of red blood cells to the supplied organ area being effectively interrupted. A further disadvantage is that the refractive index of the common salt solution is roughly equal to that of blood plasma. The same applies for the x-ray contrast medium. Thus the existence of significant differences in the refractive index, leading to adverse scattering effects, continues to be a problem.

An object of the invention is therefore to specify a method that enables imaging to be improved whilst at the same time ensuring adequate blood supply to the organ area supplied by the vessel being investigated.

To resolve this problem it is proposed, in a method according to the invention as mentioned above, that a fluid containing a medium having a higher refractive index than blood plasma and/or cytoplasm be injected, via the catheter, into the vascular area to be recorded, to enable imaging to be carried out. This fluid would be a mixture of autologous blood and the medium.

The invention is based on the finding that the given difference in the refractive index between cytoplasm and blood plasma, which causes the scattering effects described above can be reduced—or, ideally—fully compensated, by the targeted addition of a medium with a refractive index that is significantly higher than that of blood plasma and/or of cytoplasm. For example, the intracellular refractive index—i.e. that of cytoplasm in the area of the visible light—is approximately 1.465, whilst the extracellular refractive index—i.e. that of blood plasma within the visible light—is approximately 1.33. The refractive index of a medium applicable according to the invention, such as—for example—the polymeric sugar dextran, is approximately 1.52, so that the difference in refractive index can evidently be reduced, or—ideally—compensated, by adding the medium as appropriate. There are, however, other suitable media that may be used.

In order to guarantee an improvement in the blood supply to the regions downstream of the vascular area being investigated, as well as improving the quality of the images recorded, a particularly advantageous first embodiment of the invention provides for the fluid to be a mixture of autologous blood and the medium. The advantage of this is that, despite the medium for compensating the refractive index being injected, a sufficient quantity of red blood cells continues to be conveyed through the vessel, even during the investigation. The red blood cells act as oxidants, so that sections of the vessel downstream of the area being investigated can continue to be supplied, and therefore oxidant transportation is not materially impaired. Furthermore, it is possible by this means for the mixture of autologous blood and the medium, which is more or less "transparent" for the purposes of coherence tomography as a result of the alignment of the refractive indexes, to be injected in relatively large quantities over a longer period without the need to attend to any adverse effect on the patient.

It is particularly advisable for the autologous blood to be taken prior to the injection using the already inserted catheter, and mixed with the medium to produce the fluid to be injected. The autologous blood is therefore taken immediately before the injection, using the catheter, which is already in position, with the benefit that a second intervention for the purpose of taking blood is not required. The catheter has a corresponding withdrawal facility for this purpose; for example, a second lumen is provided in which blood can be drawn in and withdrawn via an external syringe, which is coupled to the lumen.

It is particularly advisable for the fluid, which—with regard to the refractive index—has been appropriately adjusted in terms of the selected mixing ratio between autologous blood and medium, to be delivered in a manner whereby said fluid entirely fills the vessel in the vascular area to be recorded. The advantages of this are that, firstly, the fluid can be optimally mixed extracorporeally according to requirements, and, secondly, it ensures that the properties of said fluid are not altered, when it is injected, by the incoming flow of autologous blood.

In one alternative, only the medium with the higher refractive index is to be used as the fluid. It would then be expedient for this fluid to be delivered in a manner whereby it mingles with the autologous blood flowing into the vascular area to be recorded. The more or less "transparent" mixture for OCT purposes is therefore produced intracorporeally in this case, by the local mixing of the medium and the autologous blood immediately before the vascular area to be investigated. To enable an optimum mixture to be produced for the purpose of achieving extensive index alignment with regard to the given refractive indexes, the delivery of the medium to be mixed with the autologous blood must be carried out in a suitably controlled manner. For this purpose it is advisable for the quantity of fluid delivered per unit of time to be determined according to the quantity of blood perfusing the vessel per unit of time in the vascular area to be recorded. The incoming quantity of blood can be determined relatively accurately, so that the quantity of fluid injected per unit of time can be administered with correspondingly precise dosage.

As described, it is advisable to use a polymeric sugar solution as the medium; in this case dextran is used in preference. The particular advantage of using dextran is that it is a long-chain molecule, which is not metabolized, and can therefore also be administered—for example—to diabetics and other patients with an intolerance to sugar.

Particularly in the alternative form, in which the fluid consists solely of the medium, it is advisable for the fluid to be released at an angle to the longitudinal axis of the vascular wall to ensure that the fluid is mixed effectively and homogeneously with the autologous blood. The fluid can thus be released in a direction essentially at right angles to the vascular wall, so that it flows outward in a more or less radial manner, preferably via a plurality of openings arranged around the periphery of the catheter and which may also be arranged lengthwise along the catheter. Since the autologous blood flows longitudinally along the vessel, and therefore in a direction that is more or less perpendicular to the outflow direction, a highly effective, rapid and homogeneous mixing effect is produced. It is particularly advantageous if the fluid is released, by a correspondingly designed catheter, in a direction somewhat contrary to the blood flow, in other words almost opposite to the direction of the autologous supply.

In addition to the method according to the invention, the invention also relates to a catheter for use in the described method, characterized in that it has a first lumen in which the image recording unit is carried in the form of an optical fiber, and a second lumen, which has a plurality of outlet openings distributed around the periphery of the catheter for the fluid delivered by said second lumen.

These outlet openings can also be distributed along the length of the catheter in order to create a larger outlet area (from the surface perspective) so that the fluid—regardless of whether it is a mixture of autologous blood and the medium, or the medium alone—can be delivered quickly and in sufficient quantity, and also in order to generate an extensive mixing area if the fluid delivered is to be mixed with incoming autologous blood.

The outlet openings can be configured such that the fluid can be released outward in a direction essentially perpendicular to the longitudinal direction of the catheter. Alternatively, they may also be arranged or configured such that the delivered fluid is deflected and can be released outward in a direction that is essentially contrary to the supply direction. The second lumen actually surrounds the first lumen completely and in an essentially symmetrical manner, to advantageous effect.

BRIEF DESCRIPTION OF THE DRAWINGS

Other advantages, features and details of the invention are described in the following exemplary embodiments, with the help of diagrams, in which.

DETAILED DESCRIPTION OF INVENTION

Figure 1:
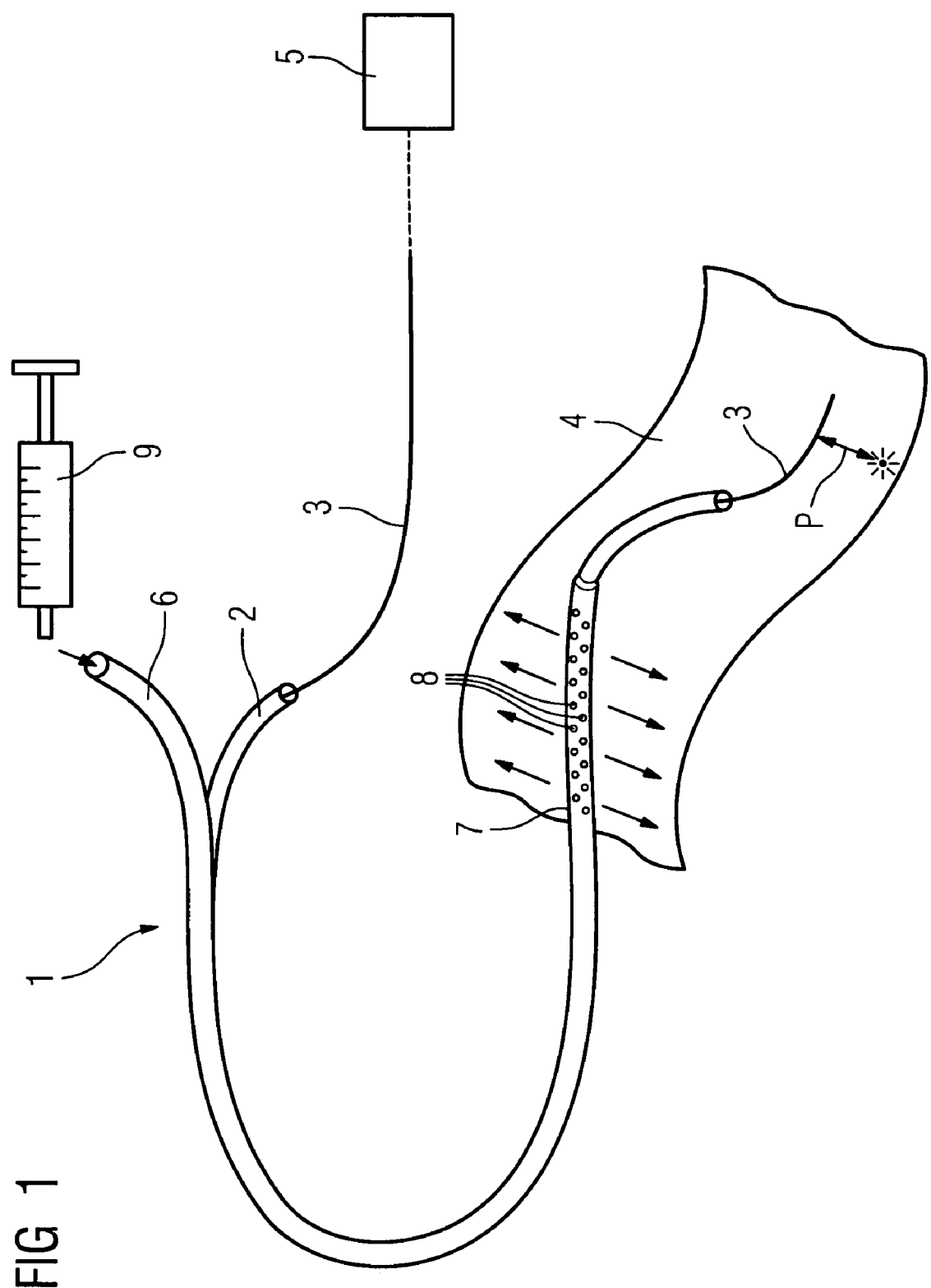
FIG. 1 shows a representative illustration of a catheter for implementing the method according to a first embodiment.

FIG. 1 shows a catheter 1 according to the invention, comprising a first lumen 2, in which the movement of an imaging device 3 in the form of a wire with an integrated optical fiber (not shown in greater detail) is guided for the purpose of recording images from a vessel in an optical coherence tomography procedure. This image recording unit 3, i.e. the wire, protrudes out of the front, open end of the lumen 2, as shown in FIG. 1. In this area there is a window via which light delivered via the optical fiber (not shown in greater detail) is radiated onto the tissue of the vessel 4, which is illustrated here as being opened out for the sake of clarity, and via which light reflected from the vascular wall is coupled back into the optical fiber and carried to the exterior, where it is supplied to a control and processing unit 5 (shown here in exemplary form only) in order to generate the coherence tomography images. The light emission and coupling of the reflected light is illustrated by the double-ended arrow P.

Figure 3:
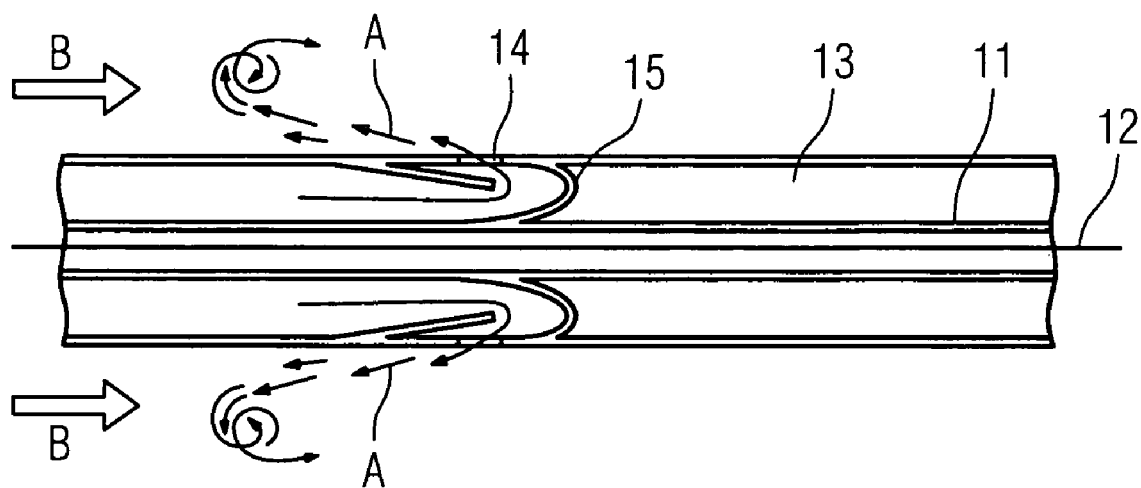
FIG. 3 shows an enlarged partial view of the catheter from FIG. 3.

The catheter according to the invention also has a second lumen 6, which—as described in greater detail below with reference to FIG. 3—completely and symmetrically surrounds the first lumen. This lumen is used to deliver an injected fluid, which is to emerge in an area of the vessel to be investigated located just before the actual area to be imaged. For this purpose a large number of openings 8, from which the delivered fluid can emerge, are provided in the outer sheath 7 of the catheter, said openings being distributed circumferentially and longitudinally along the catheter. The lumen is closed toward its front end so that the fluid cannot escape in a forward direction; instead, the fluid essentially emerges radially from the lumen if viewed in cross-section so that the lumen appears circular in shape.

In the example shown, the fluid is delivered using a syringe 9, which can be connected to the second lumen 6. This may be done according to different procedures.

Either the autologous blood is removed first, using the syringe, via the outlet openings 8 in the second lumen following the introduction of the catheter; in other words the outlet openings 8 are in this case being used as inlet openings for the blood. Once a sufficient quantity of autologous blood, e.g. 25 ml, has been taken, the autologous blood is mixed—for example by shaking—with the medium for increasing the refractive index or for compensating differences in the refractive index, whereby said medium—for example dextran—is already present in the syringe 9 when the blood is taken. The quantity of the means similarly amounts to 25 ml for example. A blood-medium mixture is therefore produced immediately before the injection. This mixed fluid is then reinjected into the second lumen 6, so that it can emerge via the outlet openings 8. The quantity of fluid delivered is measured to ensure that it completely fills the vessel in the area of investigation, which means that the autologous blood supply from a vascular area located before said area of investigation is interrupted for the duration of the imaging process by the corresponding delivery of fluid. There are no disadvantages to this since the injected fluid delivered contains autologous blood, and therefore also red blood cells, which are responsible for transporting oxygen, so that the supply to the vascular regions located downstream of the parts of the vessel being investigated is guaranteed.

As an alternative to the removal of autologous blood and production of the mixture, the delivered fluid may also consist solely of the medium, for example dextran. To ensure that the downstream vascular area or organs continue to be supplied during the imaging process, despite the dextran injection, in this case the medium is administered in a dose that enables it to be mixed, within the vessel, with the incoming flow of autologous blood. A homogeneous mixing effect is achieved due to the essentially radial release direction of the medium, whereby the autologous blood, which flows parallel to the longitudinal axis of the catheter and thus to the longitudinal axis of the vessel, essentially meets the emerging fluid at right angles, resulting in homogeneous and rapid mixing. The quantity of fluid administered must be measured so that the correct mixing ratio between autologous blood and administered medium is produced with reference to the quantity of incoming autologous blood per unit of time, so that the mixing effect to be achieved in the area to be imaged is adjusted to best possible effect with regard to the refractive indexes. As in the case of extracorporeal mixing, this procedure likewise involves dilution of the blood and therefore reduces the blood cell count whilst at the same time aligning the refractive indexes of the blood plasma and cytoplasm.

Figure 2:
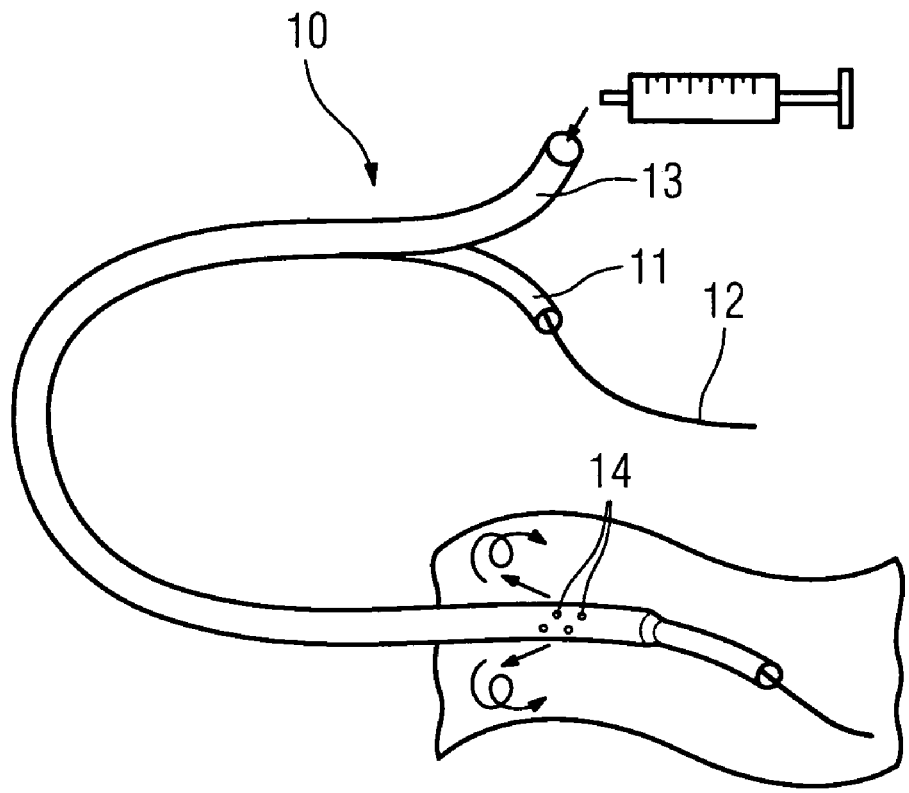
FIG. 2 shows a representative illustration of a catheter for a second embodiment.

FIG. 2 shows an inventive catheter 10 according to a second embodiment, which, in its basic form, essentially corresponds to the catheter 1 shown in FIG. 1. It likewise has a first lumen 11 containing a movable imaging device 12 in the form of the OCT wire. It also has a second lumen 13, which is used for the delivery of fluid (and possibly also for the prior withdrawal of blood).

The design of the second lumen 13, however, differs somewhat from the second lumen in the catheter 1 according to FIG. 1, the difference being in the location of the outlet openings 14. As shown by the enlarged detailed view in FIG. 3, a deflection device 15 is connected in series or assigned in each outlet opening 14. This has the effect of deflecting the fluid delivered as shown by the arrow A so that it is released in a direction that is essentially contrary to the direction of the blood supply. Since the blood supply as shown by the arrow B flows virtually in the opposite direction, the resulting strong intermingling effect generates a turbulence, so that the fluid, in this case—for example—the pure dextran, is mixed quickly and homogeneously with the autologous blood supply. Deflecting the release of the fluid with regard to the outlet direction, however, is useful not only for the delivery of fluid in the form of pure dextran. If a blood-dextran mixture is delivered, the fluid is dosed to ensure that it completely fills the vessel, which means that the autologous blood supply, as shown in FIG. 3 by the arrow B, is almost completely halted by the injection of a sufficient quantity of fluid. The contrary direction of the outward flow forms a barrier at which the autologous blood supply is virtually "stopped".

The invention claimed is:

1. A method of recording a two-dimensional image of a perfused blood vessel of a patient using a catheter having an integrated imaging device adapted to emit light and record light reflected from a vascular wall of the blood vessel, the method comprising:
   injecting a fluid into an examination area of the blood vessel using the catheter, wherein the injecting the fluid into the examination area includes filling the blood vessel entirely with the fluid in the examination area;
   recording the two-dimensional image by the image device, wherein the fluid comprises autologous blood comprising red blood cells drawn from the patient and a fluid component having a higher refractive index than the autologous blood;
   prior to the injecting, inserting the catheter into the blood vessel and drawing the autologous blood from the patient; and
   prior to the injecting, producing the fluid extracorporeally by mixing the drawn blood with the fluid component.

2. The method according to claim 1, wherein the fluid component comprises a polymeric sugar solution.

3. The method according to claim 2, wherein the polymeric sugar is Dextran.

4. The method according to claim 1, wherein the fluid is injected into the blood vessel at an angle relative to a longitudinal axis of the blood vessel in a direction towards the vascular wall.

5. The method according to claim 4, wherein the angle is substantially 90°.

6. The method according to claim 4, wherein the direction includes a direction vector component opposite to a blood stream direction within the blood vessel.

7. The method according to claim 1, wherein the fluid is injected into the blood vessel via a plurality of outlet openings arranged around the catheter periphery.

8. The method according to claim 1, wherein the fluid is injected into the blood vessel via a plurality of outlet openings arranged on the catheter in a direction parallel to a longitudinal axis of the catheter.

* * * * *